United States Patent
Chen et al.

(10) Patent No.: US 12,358,809 B2
(45) Date of Patent: Jul. 15, 2025

(54) DEVICE AND METHOD FOR PRODUCING NANO-SIZED ZINC MOLYBDATE AND APPLICATION OF SAME

(71) Applicant: HUBEI ZHONG'AO NANOTECH CO., LTD, Guangshui (CN)

(72) Inventors: Fangwu Chen, Guangshui (CN); Xu Zhao, Guangshui (CN); Luocheng Chen, Guangshui (CN); Zheng Sun, Guangshui (CN); Zhongkai Wu, Guangshui (CN); Zhen Chen, Guangshui (CN)

(73) Assignee: HUBEI ZHONG'AO NANOTECH CO., LTD, Guangshui (CN)

( * ) Notice: Subject to any disclaimer, the term of this patent is extended or adjusted under 35 U.S.C. 154(b) by 730 days.

(21) Appl. No.: 17/667,511

(22) Filed: Feb. 8, 2022

(65) Prior Publication Data
US 2022/0162088 A1 May 26, 2022

Related U.S. Application Data

(63) Continuation of application No. PCT/CN2020/089537, filed on May 11, 2020.

(30) Foreign Application Priority Data

Aug. 9, 2019 (CN) .......................... 201910736311.7

(51) Int. Cl.
*C01G 39/02* (2006.01)
*A61K 33/30* (2006.01)
(Continued)

(52) U.S. Cl.
CPC .............. *C01G 39/02* (2013.01); *A61K 33/30* (2013.01); *B82Y 30/00* (2013.01); *B82Y 40/00* (2013.01); *C01P 2004/64* (2013.01)

(58) Field of Classification Search
None
See application file for complete search history.

(56) References Cited

U.S. PATENT DOCUMENTS

| 5,009,675 A | * | 4/1991 | Kunz | ..................... C04B 41/009 |
| | | | | 51/293 |
| 2014/0308489 A1 | * | 10/2014 | Miyahira | ................ B32B 27/20 |
| | | | | 428/206 |
| 2016/0251522 A1 | * | 9/2016 | Liu | ......................... C23C 16/56 |
| | | | | 428/220 |

FOREIGN PATENT DOCUMENTS

| CN | 101905495 A | 12/2010 |
| CN | 106496884 A | 3/2017 |

(Continued)

OTHER PUBLICATIONS

English translation of JP-2005082668-A Description. (Year: 2005).*

(Continued)

*Primary Examiner* — Anthony J Zimmer
*Assistant Examiner* — Zachary John Baum

(57) ABSTRACT

A production device, method and application of nano-sized zinc molybdate. The device includes a double-cone mixer; an elevator is obliquely provided at a bottom of a discharge port of the double-cone mixer; a rear end of the elevator is located above a feeder; the feeder is connected to one end of an electric heating converter, an other end of the electric heating converter is connected to a finished product bin; a top of the finished product bin is provided with an atomizing nozzle for adding nanomaterial dispersant; the atomizing nozzle is connected to a syringe pump by pipeline. High-purity nano-sized molybdenum trioxide and nano-sized zinc oxide are adopted to synthesize nano-sized zinc molybdate in an electric heating converter. The nano-sized zinc molybdate prepared by the device and method can be used for (Continued)

treatment of African swine fever virus, coronavirus, and AIDS phase I, Ebola, dengue fever, polio viruses.

2 Claims, 1 Drawing Sheet

(51) Int. Cl.
  *B82Y 30/00* (2011.01)
  *B82Y 40/00* (2011.01)

(56) References Cited

FOREIGN PATENT DOCUMENTS

| | | | | |
|---|---|---|---|---|
| CN | 107337839 A | 11/2017 | | |
| CN | 108017088 A | 5/2018 | | |
| CN | 110304656 A | 10/2019 | | |
| GB | 1379122 A | * 1/1975 | ............. | C01G 39/00 |
| JP | 2005082668 A | * 3/2005 | | |
| RU | 2008263 C1 | 2/1994 | | |

OTHER PUBLICATIONS

Internation Search Report of PCT/CN2020/103599, Mailed Aug. 5, 2020.
Yu. Hizhnyi et al., "Origin of luminescence in ZnMoO4 crystals: Insights from spectroscopic studies and electronic structure calculations", Journal of Luminescence, vol. 211.Mar. 19, 2019, ISSN: 0022-2313, p. 128 left-hand col. lines 8-23.

* cited by examiner

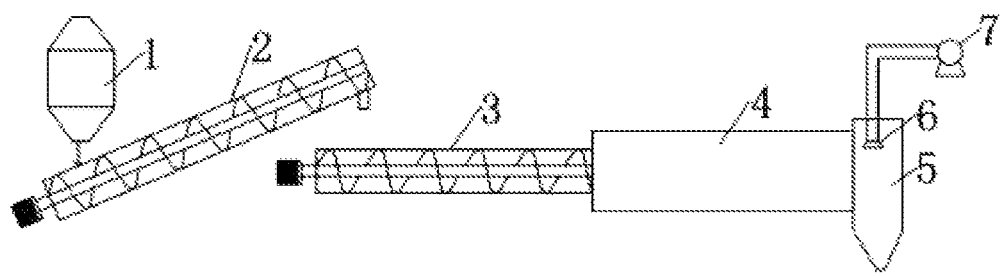

DEVICE AND METHOD FOR PRODUCING NANO-SIZED ZINC MOLYBDATE AND APPLICATION OF SAME

CROSS-REFERENCE TO RELATED APPLICATIONS

This application is a continuation of International Patent Application No. PCT/CN2020/089537, filed on May 11, 2020, which claims the benefit of priority of Chinese Application No. 201910736311.7, filed on Aug. 9, 2019. The content of the aforementioned applications, including any intervening amendments thereto, are incorporated herein by reference.

TECHNICAL FIELD

The present disclosure relates to the technical field of production of zinc molybdate, in particular to device and method for producing nano-sized zinc molybdate and application of same.

BACKGROUND

In industry, zinc molybdate is generally synthesized by mixing industrial-grade molybdic acid with zinc oxide in a converter at 600-700° C. The synthesized zinc molybdate is insoluble in water and has a particle size of 8-10 um. It is generally used as corrosion inhibitor, anti-rust pigment, flame retardant and smoke suppressant, oil additive, metal corrosion inhibitor for pollution-free cooling water system, and trace ingredients necessary for animals and plants. In recent years, organic antibiotics have been overused, resulting in serious secondary pollution and endless troubles. Moreover, fungicides of inorganic silver, zinc, copper and other ionic are being popularized and applied. However, silver ions have a too strong bactericidal performance, such that the beneficial bacteria in the environment will be destroyed. Therefore, it is classified in a strictly controlled use category in the United States. Hence, zinc, copper and other ion salts are an important development direction in the future.

Professor Wenzheng Zhang and his team from Northwestern Polytechnical University, based on the principle of the non-polarity of zinc molybdate molecules, which can release zinc ions but the molecules are stable, have conducted many years of research and found that the smaller the zinc molybdate particles are, the more significant the effect is, and the same effect can be achieved when the percentage of nano-sized zinc molybdate is reduced below 10-100 ppm. The nano-sized zinc molybdate can improve the environment and save resources. The molybdate ions and zinc ions released by the zinc, molybdate particles during use can kill bacteria and form stable zinc molybdate molecules, which last for up to 15 years.

Therefore, how to prepare zinc molybdate with finer particle size and higher purity is the problem to be solved by the present disclosure.

SUMMARY

In order to overcome the above deficiencies of the prior art, the present disclosure provides a production device, method and application of nano-sized zinc molybdate, which solves the problems of environmental pollution, large particle size of zinc molybdate and inability to achieve large-scale zinc molybdate preparation in the prior art.

The present disclosure is achieved through the following technical solutions.

A production device for nano-sized zinc molybdate, comprising a double-cone mixer; an elevator is provided at a bottom of a discharge port of the double-cone mixer; the elevator is obliquely arranged; a rear end of the elevator is located above a feeder; the feeder is connected to one end of an electric heating converter, an other end of the electric heating converter is connected to a finished product bin; and a top of the finished product bin is provided with an atomizing nozzle for adding nanomaterial dispersant, and the atomizing nozzle is connected to a syringe pump by pipeline.

Further, the electric heating converter is made of 2520 material.

Further, the syringe pump is a medical metering syringe pump.

Further, the feeder is a quantitative metering feeder.

A method for producing nano-sized zinc molybdate by using, the production device, comprising following steps: fully mixing high-purity nano-sized molybdenum trioxide and nano-sized zinc oxide with a mol ratio of 1:1.02 in the double-cone mixer; feeding, by the elevator and the feeder, the mixture into the electric heating converter for synthesis reaction to obtain the nano-sized zinc molybdate; wherein a reaction temperature is 460±1° C. reaction time is 40 min; transferring the obtained nano-sized zinc molybdate into the finished product bin; and spraying, by the atomizing nozzle connected to the syringe pump, the nanomaterial dispersant to the finished product bin, and finally obtaining finished product of nano-sized zinc molybdate.

Further, the electric heating converter is provided with a plurality of heating zones, and the reaction time in high temperature zone is 10 min.

Further, a particle diameter of the nano-sized zinc molybdate is between 25-120 nm.

An application of the nano-sized zinc molybdate produced by the method in prevention, treatment of African swine fever virus and coronavirus, and AIDS phase I, Ebola, dengue fever, and poliomyelitis viruses.

The present disclosure achieves following beneficial effects.

In the device and method for producing the nano-sized zinc molybdate of the present disclosure, high-purity nano-sized molybdenum trioxide and nano-sized zinc oxide are adopted to synthesize the nano-sized zinc molybdate in an electric heating converter. The method is easy to operate and control, and has no emission and the utilization rate of molybdenum oxide is nearly 100%. The nano-sized zinc molybdate can be produced on an industrial scale. The nano-sized zinc molybdate prepared by the device and method of the present application can be used for the treatment of African swine fever virus, and is also effective in fighting coronavirus, and AIDS phase I, Ebola, dengue fever, and poliomyelitis and other RNA viruses. Compared with the existing common fungicides, the nano-sized zinc molybdate has a better and quicker bactericidal effect.

BRIEF DESCRIPTION OF THE DRAWINGS

The single FIGURE is a schematic structural diagram of a production device for nano-sized zinc molybdate according to an embodiment of the present disclosure.

In the FIGURE: 1, double-cone mixer; 2, elevator; 3, feeder; 4, electric heating converter; 5, finished product bin; 6, atomizing, nozzle; and 7, syringe pump.

DETAILED DESCRIPTION OF PREFERRED EMBODIMENTS

The embodiments are used to specifically illustrate the disclosure and should not be construed to limit the scope of the disclosure. Modifications to the present disclosure may be made simultaneously in terms of materials, methods and reaction conditions, all of which should fall within the spirit and scope of the present disclosure.

As shown in the FIGURE, a production device for nano-sized zinc molybdate including a double-cone mixer 1, a bottom of a discharge port of the double-cone mixer 1 is provided with an elevator 2, and the elevator 2 is arranged obliquely. A rear end of the elevator 2 is located above a feeder 3, the feeder 3 is connected to one end of an electric heating converter 4, an other end of the electric heating converter 4 is connected to a finished product bin 5, and the electric heating converter 4 is made of material of 2520. A top of the finished product bin 5 is provided with an atomizing nozzle 6 for adding nanomaterial dispersants. The atomizing nozzle 6 is connected to a syringe pump 7 through a pipeline.

In this embodiment, the syringe pump 7 is a medical metering syringe pump.

In this embodiment, the feeder 3 is a quantitative metering feeder.

A method for producing nano-sized zinc molybdate, including following steps: adding high-purity nano-sized molybdenum trioxide and nano-sized zinc oxide into the double-cone mixer 1 with a molar ratio of 1:1.02 to fully mix; sending the mixture into the electric heating converter 4 for synthesis reaction through the elevator 2 and the feeder 3 to obtain the nano-sized zinc molybdate; wherein a reaction temperature is 460±1° C., a reaction time is 40 min; transferring the obtained nano-sized zinc molybdate into the finished product bin 5; and spraying the nanomaterial dispersant to the finished product bin 5 through the atomizing nozzle 6 connected to the syringe pump 7, and finally obtaining finished product of nano-sized zinc molybdate.

In this embodiment, the electric heating converter 4 is provided with a plurality of heating zones, and the reaction time in high temperature zone is 10 min.

In this embodiment, a particle diameter of the nano-sized zinc molybdate is between 25-120 nm.

In the method, high-purity nano-sized molybdenum trioxide and nano-sized zinc oxide are adopted to synthesize nano-sized zinc molybdate in an electric heating converter. The method is easy to operate and control, and has no emission and the utilization rate of molybdenum oxide is nearly 100%. The nano-sized zinc molybdate can be produced on an industrial scale.

An application of the nano-sized zinc molybdate in the prevention and treatment of African swine fever virus. Direction for use is as follows: take nano-sized zinc molybdate with a concentration of 100 ppm by mouth; alternatively, inject 3-8 ml of nano-sized zinc molybdate injection with a concentration of 0.5% prepared by mixing nano-sized zinc molybdate with distilled water into a pig (the dosage is adjusted according to a weight of the pig).

The specific antivirus principle: first, a size of African swine fever virus is 175-215 nm, while a size of general bacteria is 270 nm, the African swine fever virus is two-thirds of the volume of ordinary bacteria; second, African swine fever virus has a cyst membrane; third, many lipid solvents and bactericides can destroy the cyst membrane. The nano-sized zinc molybdate has a fast metabolism in pigs and is safe. Due to a high electrode energy of the cyst membrane, when zinc molybdate molecules touch the cyst membrane of virus, the zinc molybdate molecules are dissociated into molybdate ion and zinc ion, which quickly pierce the cyst membrane of the virus, until the virus dies. If there is no virus, the zinc molybdate molecule is automatically synthesized, and the dissociation and synthesis are in an infinite loop. As long as it is not lost, the validity period of the nano-sized zinc molybdate can reach 15 years. Nano-sized copper molybdate has the same effect in killing swine fever virus.

An application of the nano-sized zinc molybdate in fighting coronavirus, and AIDS phase I, Ebola, dengue fever, polio and other RNA viruses. The nano-sized zinc molybdate particle has a particle size between 25-120 nm, and is a hard agglomerated nano-scale particle formed by about 100 zinc molybdate molecules. Since the valences of molybdenum are +2, +3, +4, +5, +6, steady-state molybdate ions can be formed at different valences. In a body fluid environment, molybdenum atoms easily escape electrons, or several molybdenum atoms share one outer electron, so the nano-sized zinc molybdate can easily release zinc ions under certain conditions. When the released zinc ions react in contact with microorganisms, the inherent components of the microorganisms are destroyed or dysfunction is occurred (the replication of genetic material is inhibited), thereby resulting in the death of bacteria and fungi. For viruses, the nano-sized zinc molybdate is broad-spectrum and has drug resistance. The nano-sized zinc molybdate has a fast metabolism in the human body and is safe. When nano-sized zinc molybdate particles enter the infected cells, zinc ions cause viral protein poisoning, and molybdate ions inhibit the activity of viral synthase, both of which work together to kill viruses.

The above description is only an embodiment of the present disclosure, and is not intended to limit the scope of the present disclosure. Any equivalent structure or equivalent process modification made by using the contents of the description and drawings of the present disclosure, directly or indirectly applied to other related technologies fields, are included in the protection scope of the present disclosure.

The invention claimed is:

1. A method for producing nano-sized zinc molybdate by using a production device, the production device comprising-comprises a double-cone mixer (1);
   wherein an elevator (2) is provided at a bottom of a discharge port of the double-cone mixer (1);
   the elevator (2) is obliquely arranged; a rear end of the elevator (2) is located above a feeder (3);
   the feeder (3) is connected to one end of an electric heating converter (4), an other end of the electric heating converter (4) is connected to a finished product bin (5); and a top of the finished product bin (5) is provided with an atomizing nozzle (6) for adding nanomaterial dispersant, and the atomizing nozzle (6) is connected to a syringe pump (7) by pipeline;
   the method comprising the following steps:
   fully mixing molybdenum trioxide and zinc oxide with a mol ratio of 1:1.02 in the double-cone mixer (1);
   feeding, by the elevator (2) and the feeder (3), the mixture into the electric heating converter (4) for synthesis reaction to obtain the nano-sized zinc molybdate; wherein a particle diameter of the nano-sized zinc molybdate is between 25-120 nm, a reaction temperature is 460±1° C., a reaction time is 40 min;
   transferring the obtained nano-sized zinc molybdate into the finished product bin (5); and spraying, by the atomizing nozzle (6) connected to the syringe pump (7), the nanomaterial dispersant to the finished product bin (5), and finally obtaining finished product of nano-sized zinc molybdate.

2. The method of claim 1, wherein the electric heating converter (4) is provided with a plurality of heating zones, and the reaction time in high temperature zone is 10 min.

* * * * *